(12) United States Patent
Muramatsu et al.

(10) Patent No.: US 6,485,916 B2
(45) Date of Patent: Nov. 26, 2002

(54) PREPARATION METHOD OF NUCLEIC ACID SAMPLE FOR RARE EXPRESSED GENES AND ANALYZING METHOD USING THE PREPARED NUCLEIC ACID SAMPLES THEREBY

(75) Inventors: Takamichi Muramatsu, Shiki (JP); Takeshi Fujita, Hiki-gun (JP); Masaharu Kiyama, Higashimatsuyama (JP); Takashi Irie, Musashimurayama (JP); Kazunori Okano, Shiki (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/788,338

(22) Filed: Feb. 21, 2001

(65) Prior Publication Data

US 2002/0102561 A1 Aug. 1, 2002

Related U.S. Application Data

(63) Continuation of application No. 09/313,637, filed on May 18, 1999.

(30) Foreign Application Priority Data

May 20, 1998 (JP) .......................................... 10-153651

(51) Int. Cl.$^7$ ................................................ C12Q 1/68
(52) U.S. Cl. ............................ 435/6; 435/5; 435/91.1; 435/91.2; 435/183; 435/252.3; 536/25.4; 536/25.3
(58) Field of Search ............................. 435/6, 5, 91.1, 435/91.2, 183, 252.2; 536/25.4, 25.3

(56) References Cited

U.S. PATENT DOCUMENTS 5,888,792 A * 3/1999 Bandman et al. ........... 435/183

6,180,778 B1 * 1/2001 Bastian et al. ............. 536/25.4

OTHER PUBLICATIONS

Analytical Biochemistry, vol. 162, 1987, P. Chomczynski et al, pp. 156–159.

Nucleic Acids Research, 1995, vol. 23, No. 21, D. J. Bertioli et al, pp. 4520–4523.

FEBS Letters, 1994, T. Ito et al, pp. 231–236.

Nucleic Acids Research, vol. 18, No. 19, M. Ko et al, pp. 5705–5711.

Science, vol. 257, Aug. 14, 1992, P. Liang et al, pp. 967–971.

Nucleic Acids Research, 1995, vol. 23, No. 18, K. Kato, pp. 3685–3690.

Science, vol. 270, Oct. 20, 1995, V. Velculescu et al, pp. 484–487.

Molecular Cloning A Laboratory Manual, Second Edition, Cold Spring Harbor Laboratory Press, 1989, J. Sambrook et al, "Synthesis of the First Strand of cDNA & Amplification of cDNA Generated by Reverse Transcription of mRNA".

Molecular Biology of the Cell, Second Edition, Garland Publishing, Inc., B. Alberts et al, "RNA Synthesis and RNA Processing".

* cited by examiner

*Primary Examiner*—W. Gary Jones
*Assistant Examiner*—Janell E. Taylor
(74) *Attorney, Agent, or Firm*—Mattingly, Stanger & Malur, P.C.

(57) ABSTRACT

Focusing that abundant class genes abundantly present in a nucleic acid sample can comparatively easily be analyzed and readily be removed in a selective manner, a nucleic acid sample for expression analysis of rare expressed genes can be obtained by removing abundant genes therefrom, and analyses based upon the sample can be achieved.

8 Claims, 9 Drawing Sheets

FIG. 2B ↓ Add Probes

FIG. 2D ↓ Add Ribonuclease H

— AAAAAAAAA

FIG. 2F ↓ Inactivate Ribonuclease H

FIG. 2G ↓ Digest the Probes with DNase

FIG. 3B ↓ Add Probes 

↓ Add Ribonuclease H

FIG. 3F ↓ Inactivate Ribonuclease H
FIG. 3G ↓ Digest the Probes with DNase

FIG. 4B ↓ Add Oligo(dT) Primers

FIG. 4D ↓ Digest mRNA with RNase

FIG. 5B ↓ Add Probes

FIG. 5D ↓ Add Oligo(dT) Primers

FIG. 5F ↓ Digest mRNA with RNase

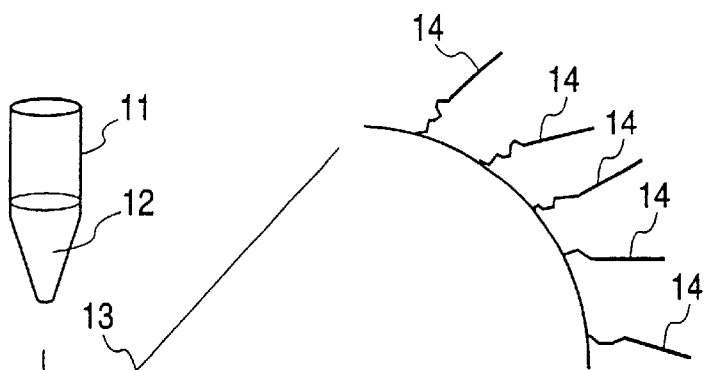
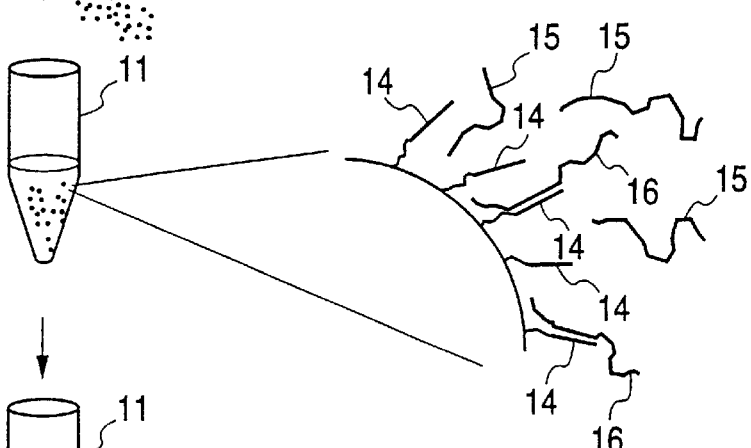
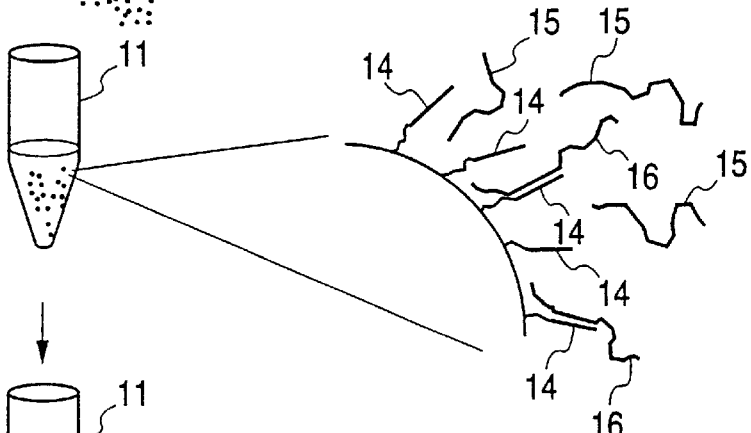
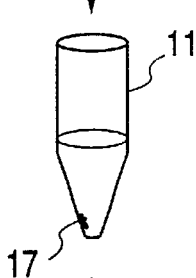
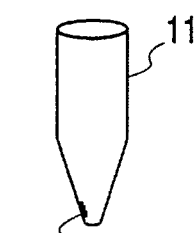
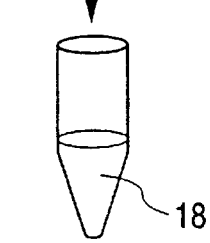

PREPARATION METHOD OF NUCLEIC ACID SAMPLE FOR RARE EXPRESSED GENES AND ANALYZING METHOD USING THE PREPARED NUCLEIC ACID SAMPLES THEREBY

This is a continuation application of U.S. application Ser. No. 09/313,637, filed May 18, 1999.

BACKGROUND OF THE INVENTION

1. Field of the Invention

The present invention relates to a preparation method of nucleic acid sample, in particular to a preparation method of nucleic acid sample suitable for analysis of rare expressed genes in the sample, to nucleic acid samples obtained by the preparation method and to an analyzing method using the prepared nucleic acid samples.

2. Description of the Related Art

Constitutive cells of a human body can be classified into 200 or more species, and each one cell type has subtly different subtypes. Each of the cells has a common genome coding for about $10 \times 10^4$ genes and several ten thousands genes are expressed therein according to its cell type. Investigations on such gene expression have become more important not only for obtaining findings on functions of individual genes but also for clarifying biological phenomena. Detailed analyses on comparatively limited few genes have revealed that plural genes operate in coordination in majority of the biological phenomena. In the course of the human genome project, investigations on networks of genes for macroscopic comprehension of relations between genes and biological phenomena are to start. Under these circumstances, demands have been made to provide techniques for further detailed analyses of a multitude of genes.

Recently, there have been developed analyzing methods of gene expression by the comparison between RNA fingerprintings (e.g., differential display method (Liang, P., and Pardee, A. B. (1992) Science 257,967–971) and molecular index method (Kikuya Kato (1995) Nucleic Acids Res., 23,3685–3690)) and methods using DNA chips, suggesting the possibility of complete analysis of expressed genes.

Expressed Genes can be roughly classified according to its expressing amount into three classes, i.e., abundant class where a gene is expressed 12,000 copies or more per cell, intermediate class where a gene is expressed about 300 copies per cell and rare class where a gene is expressed about 15 copies. In mammals, species of expressed genes amount to several ten thousands per cell and most genes belong to the rare class. In other words, expressed genes in a cell comprise enormous species of rare expressed genes coresident with extremely few species of abundant expressed genes yet expressed on three or four orders of magnitude greater than the rare expressed genes (e.g., Alberts, B., et al. (1989) Molecular Biology of the Cell, 2nd edition, Garland Publishing Inc., NY, USA).

As analyzing methods of rare expressed gene are known an equalized library (Minoru S. H. Ko (1990) Nucleic Acids Res., 18,5705–5711), methods based upon multiplex PCR (polymerase chain reaction) including the differential display method and the molecular index method, and methods using DNA chips. It is known, however, that the equalized library technique would lose information on expression amounts because the amounts of genes are made uniform among gene species; and that in an analysis using multiplex PCR such as in the differential display method a comparative PCR has a strong bias towards abundant expressed genes to result in less sensitivity than a usual PCR and thereby to fail to detect rare expressed genes (David J. Bertioli, et al. (1995) Nucleic Acids Res., 23,4520–4523).

SUMMARY OF THE INVENTION

It is, therefore, an object of the present invention to provide a preparation method of nucleic acid sample suitable for analyses of rare expressed genes, and nucleic acid samples prepared thereby, and to provide an analyzing method of rare expressed genes using the prepared nucleic acid samples.

The present inventors focused that abundant expressed gene (abundant class) in a nucleic acid sample can relatively easily be analyzed and readily removed in a selective manner, as there is a strong bias towards abundant expressed genes in the process of gene expression analysis using the differential display method, and hence the expression analysis of rare expressed genes using a nucleic acid obtained by removing abundant expressed genes in advance from a nucleic acid sample to be analyzed is expected to achieve higher precision. The present invention has been accomplished on the basis of the above findings.

BRIEF DESCRIPTION OF THE DRAWINGS

These and other features, objects, and advantages of the present invention will become apparent upon a consideration of the following description of the invention when read in conjunction with the drawings, in which:

FIGS. 2A through 2G graphically illustrate a portion of the flow of an embodiment of the latter three steps among five steps for obtaining a nucleic acid sample predominantly composed of rare expressed genes from a nucleic acid sample to be analyzed, as shown in FIG. 1;

FIGS. 3A through 3G graphically illustrate a portion of the flow of another embodiment of the latter three steps among five steps for obtaining a nucleic acid sample predominantly composed of rare expressed genes from a nucleic acid sample to be analyzed, as shown in FIG. 1;

FIGS. 4A through 4E graphically illustrate residual following the steps shown in FIGS. 2A through 2G or FIGS. 3A through 3G;

FIGS. 5A through 5G graphically illustrate the flow of a partially modified embodiment of the embodiment shown in FIGS. 2A through 2G;

FIGS. 6A through 6F graphically illustrate a portion of the flow of a still another embodiment of the latter three steps among five steps for obtaining a nucleic acid sample predominantly composed of rare expressed genes from a nucleic acid sample to be analyzed, as shown in FIGS. 2A through 2G;

DESCRIPTION OF THE PREFERRED EMBODIMENT

Figure 1:
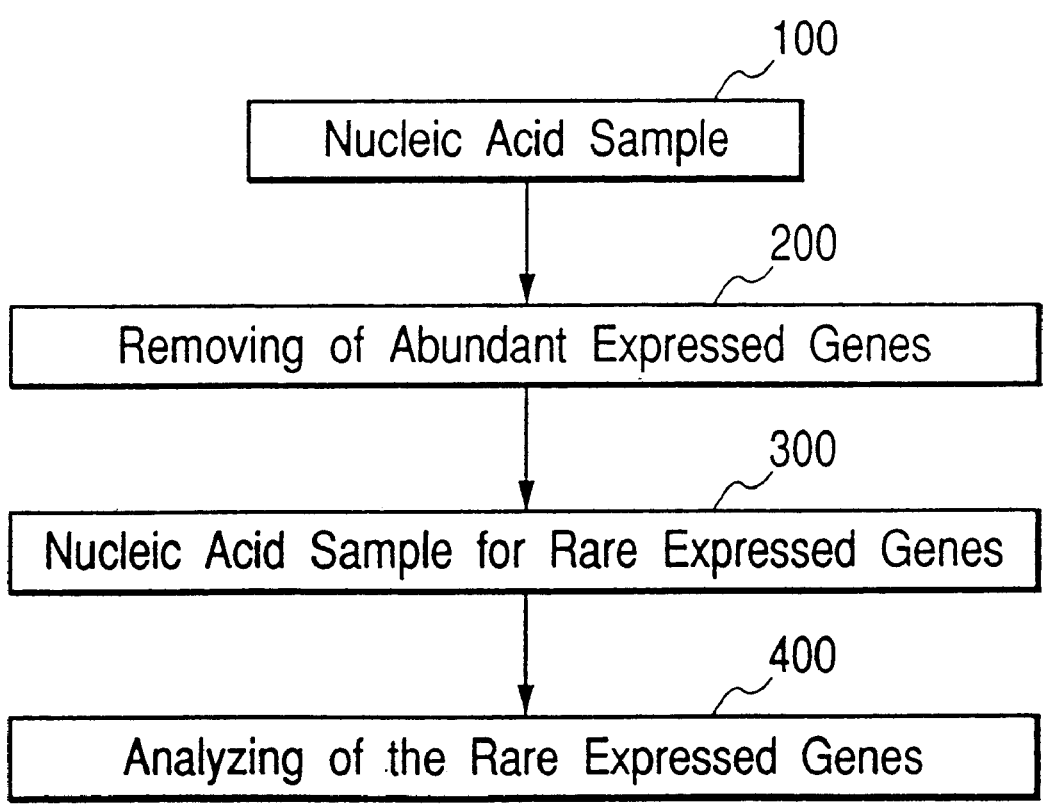
FIG. 1 graphically illustrates a fundamental procedure of an analyzing method of rare expressed genes according to the invention.

FIG. 1 graphically illustrates fundamental procedures of an analyzing method of rare expressed genes according to the invention. Process 100 is a preparing process of a nucleic acid sample to be analyzed, process 200 is a process for removing one or plural abundant expressed genes in the nucleic acid sample by adding and hybridizing probe carriers which have compliment sequence of the above genes, process 300 is a process for obtaining a nucleic acid sample predominantly composed of rare expressed genes by recovering nucleic acid sample not being hybridized with the probe carriers, and process 400 is a process for analyzing the rare expressed genes. Details of the processes 100 through 300, that is, steps for obtaining a nucleic acid sample predominantly composed of rare expressed genes from the nucleic acid sample to be analyzed are as follows:

Step 1: a preparation step of a nucleic acid sample from a biological material;

Step 2: a synthesizing step of probe carriers;

Step 3: a step of mixing and hybridizing the nucleic acid with the probe carriers;

Step 4: a step of removing genes hybridized with the probe carriers; and

Step 5: a step of recovering a nucleic acid sample for rare expressed genes.

In the above steps, the term "nucleic acid sample" means a mixture composed of, for example, mRNAs (messenger RNAs) derived from plural genes extracted from a biological material to be investigated such as cells, tissues or individuals, total RNA inclusive of mRNAs, or cDNAs (complementary DNAs) synthesized based upon mRNAs. Genes are classified according to the amounts into the abundant, intermediate and rare classes. The term "genes to be removed" in the invention means genes belonging to the abundant class and some of the intermediate class, and the term "genes to be analyzed" means genes belonging to the other of the intermediate class, and those belonging to the rare class.

Embodiments of the present invention will be described below, but they do never limit the scope of the invention.

In Step 1, any known technique according to a biological material to be subjected can be applied. By taking purification of RNA as nucleic acid sample, an AGPC method (e.g., Chomoczynski, P. and Sacchi, N. (1987) *Anal. Biochem.*, 162,156–159) can for example be applied, using a commercially available reagent such as TRIZOL Reagent (GIBCO BRL, Gaitherburg, Md., USA). A first strand cDNA can be synthesized according to the method of Sambrook, J. et al. (*Molecular Cloning: A Laboratory Manual,* 2nd ed. Cold Spring Harbor Laboratory Press, NY, USA) using a commercially available kit.

In Step 2, a gene to be removed from a nucleic acid sample (hereinafter referred to as "LEES GENE") should be selected. Information on genes which are comparatively abundantly expressed in biological materials can be obtained through, for instance, currently publicly displayed data bases such as BodyMap. BodyMap (http://www.imcb.osaka-u.ac.jp/bodymap/) is established by Kousaku Okubo, *Kenichi Matsubara et al.* (IMCB, Osaka Univ., Japan) and is a database of expressed genes for individual human tissues. Even when there is no information, such genes can be studied comparatively easily by experiments using, for example, SAGE method (Victor E. Velculescue et al. (1995) *Science,* 270,484–487). Most of LEES GENEs are expected to be so called housekeeping genes which are expressed ubiquitously in most species of cells. If only in the identical species, therefore, most of such selected gene species can be adopted to another biological material by modifying only a portion of the selected genes.

The probe sequence should be designed to meet the following conditions: that a sequence which is complementary to a portion of the sequence of the LEES GENE and is hardly hybridized with other gene should be selected; that probe carriers should not hybridized with each other; that a sequence should be selected which is hardly form intermolecular hydrogen bonds; and that the melting temperature (Tm) between the probe carrier and the target gene should be in a proper range (preferably a range from 40° to 70° C.). The configuration, material and other factors of the probe carrier vary from a removing method, and these will be described later.

In Steps 3 through 5, the following three methods can be employed. The first method, second method and third method will be further described with reference to, respectively, FIGS. 2A through 2G, 3A through 3G, 4A through 4E and 5A through 5G; FIGS. 6A through 6F, 7 and 8A through 8B; and FIG. 9. FIGS. 2A through 2G, 3A through 3G, 4A through 4E and 5A through 5G illustrate an example where LEES GENE is one gene, whereas when plural LEES GENEs should be removed, plural species of probe carriers which are obtained by designing and synthesizing individual probe carriers independently with respect to individual LEES GENEs in a nucleic acid sample are provided and the removal of the LEES GENEs can be conducted in turn.

Figure 2A:
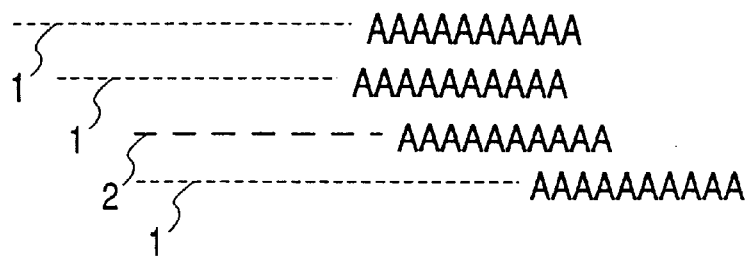

Initially, the first method will now be described in detail. The embodiment illustrated in FIGS. 2A through 2G are conducted as follows:

FIG. 2A illustrates the state of a provided nucleic acid sample, which contains plural species of rare expressed genes 1 to be remained, and gene 2 to be removed (hereinafter referred to as "LEES GENE 2". As the nucleic acid sample, a nucleic acid sample composed of mRNAs, as well as total RNA, can be employed. Although the figure gives the impression that the LEES GENE 2 is less in amount than the rare expressed genes 1 in the sample, the LEES GENE 2 belongs to the abundant class and, in actuality, occupies relatively larger part than the rare expressed genes in the sample.

FIG. 2B illiterates the step of adding a probe carrier to the provided nucleic acid sample. As the probe carrier 3 is used DNA having a sequence hybridizable with the LEES GENE 2 in the vicinity of the 3' end, or its analogue, such as one composed of PNA (peptide nucleic acid) whose 3' end is modified to inhibit elongation. Any material which has high specificity to the sequence and is recognizable by an enzyme can be used as a material of the probe carrier 3.

The probe carrier 3 used in this embodiment will be briefly described below.

Most of DNA synthesis methods using an automated synthesizer are solid phase synthesis methods in which 3' end nucleoside is bonded to a resin such as aminomethyl-polystyrene or controlled-pore glass (CPG), and after the last nucleotide is bound therewith, the obtained DNA is cut from the resin. When a probe carrier is prepared according to this method, a further modification is required to obtain a probe carrier having a modified 3' end. A DNA synthesis method, which uses a resin-bonded nucleoside having a structure as to prevent a elongation reaction, can avoid re-modification. As example of such a method, there may be mentioned a DNA synthesis method using a resin-bonded nucleoside in which the bonding site between the nucleoside and the resin is changed from 3'- to 2'-position and the hydroxyl group in the 3'-position is changed to a hydrogen atom The use of the aforementioned method therefore facilitates the synthesis of probe carriers each having modified 3' end corresponding to a variety of LEES GENEs. In addition, the application of the method to a commercially available synthesizer can provide probe carriers without the need for special instruments and techniques.

Figure 2C:
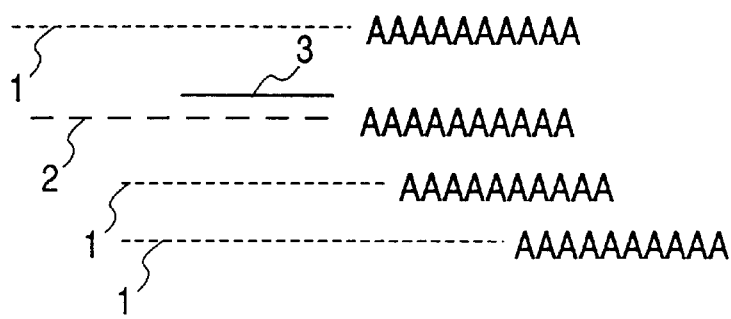

FIG. 2C illustrates the state where the probe carrier 3 is hybridized with the LEES GENE 2 in the provided nucleic acid sample. In this step, the nucleic acid sample and the probe carrier 3 are mixed in, for example, a microtube, and the mixture is allowed to stand under conditions (time, temperature of the reaction mixture, concentration of a salt, tramp materials) suitable for hybridization of the LEES GENE 2 with the probe carrier 3. In addition to a microtube, use can be made of any reactor whose wall rarely adsorbs nucleic acids and whose structure can prevent evaporation of a nucleic acid sample solution, and whose temperature can be controlled externally or internally. The condition of hybridization can be calculated using a software for probe design such as OLIGO (trade name, National Biosciences, Inc., Plymouth, Minn., USA).

FIG. 2D illustrates a treatment of adding Ribonuclease H to the nucleic acid sample in which the probe carrier 3 and the LEES GENE 2 hybridize with each other.

Figure 2E:
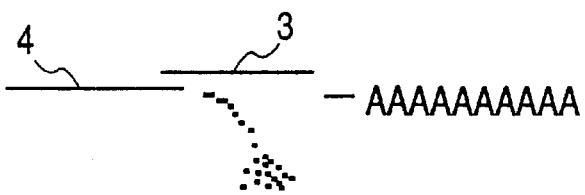

FIG. 2E illustrates the state where the sequence region of the LEES GENE 2 to which the probe carrier 3 is specifically and sufficiently hybridized is digested by the Ribonuclease H. By the digestion, the LEES GENE 2 is digested in the vicinity of 3' end to give a fragment 4. Some of Ribonuclease H have activity in a wide range of thermostability and other hybridization conditions, including *E. coli* Ribonuclease H and Thermus thermophilus Ribonuclease H (TOYOBO, Japan). Any of such Ribonuclease H can be employed depending on the hybridization conditions. In addition to Ribonuclease H, enzymes or compounds that can act and digest specifically nucleic acids hybridized with probes may be employed.

FIG. 2F illustrates an inactivation treatment of the Ribonuclease H added to the nucleic acid sample; and FIG. 2G illustrates the removal of the probe 3 from the nucleic acid sample by ,for example, treating the sample with a DNase.

A nucleic acid sample is thus prepared from which the LEES GENE 2 hybridized with the probe carrier 3 has been removed.

Next, the embodiment shown in FIGS. 3A through 3G will be illustrated below:

The treatment to the LEES GENE as illustrated in FIGS. 2A through 2G can be improved for more efficient removal by using a plurality of probe carriers. FIGS. 3A through 3G demonstrate this technique.

Figure 3A:
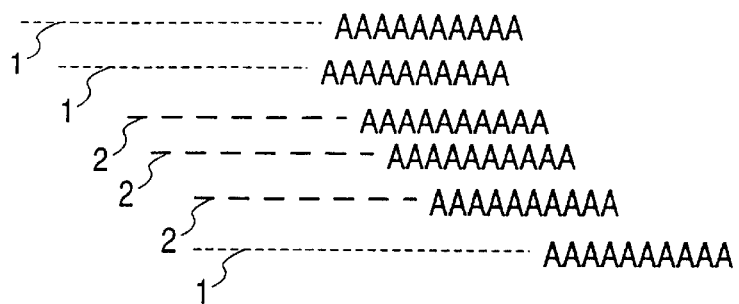

FIG. 3A illustrates the state of a provided nucleic acid sample as in FIG. 2A.

FIG. 3B illustrates, as in FIG. 2B, a treatment of adding probe carriers to the provided nucleic acid sample, whereas in this embodiment, two species of probes having different sequences are employed as the probe carriers 3 and 3'. In this treatment, as the probe carrier 3 is used DNA having a sequence hybridizable with the LEES GENE in the vicinity of the 3' end, or its analogue, such as one composed of a PNA (peptide nucleic acid), whereas as the probe carrier 3' is employed DNA having a sequence hybridizable with the LEES GENE at a site away from its 3' end, or its analogue, such as one composed of a PNA (peptide nucleic acid). Any materials which have high specificity to the sequences and are recognizable by an enzyme can advantageously be used as materials of the probe carriers 3 and 3'. The similar probe carriers to those described in FIG. 2B can preferably be employed in this embodiment.

Figure 3C:
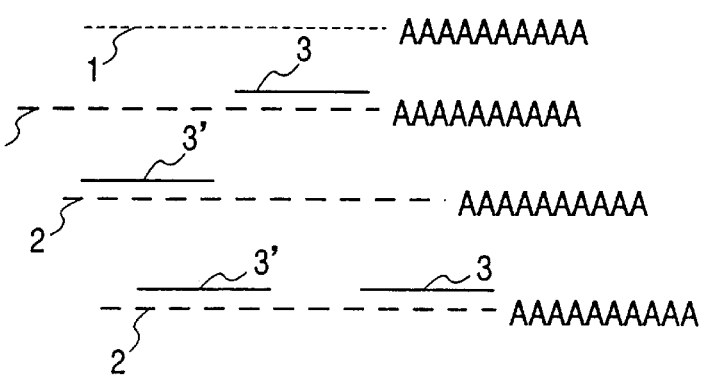

FIG. 3C illustrates, as in FIG. 2C, the state where the probe carriers are hybridized with the LEES GENE 2 in the prepared nucleic acid sample. As two species of probe carriers 3 and 3' are employed in this embodiment, there are three possible situations, i.e., with the LEES GENE 2, the probe carrier 3 is hybridized; the probe carrier 3' is hybridized; and both the probe carriers 3 and 3' are hybridized.

Figure 3D:
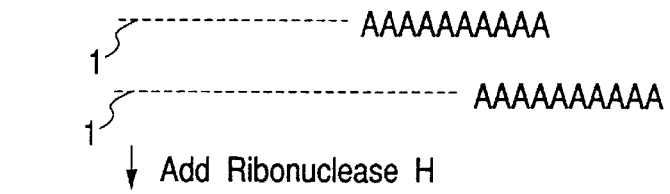

FIG. 3D illustrates, as in FIG. 2D, the treatment of adding Ribonuclease H to the nucleic acid where the probe carriers 3 and 3' and the LEES GENE 2 hybridize with each other.

Figure 3E:
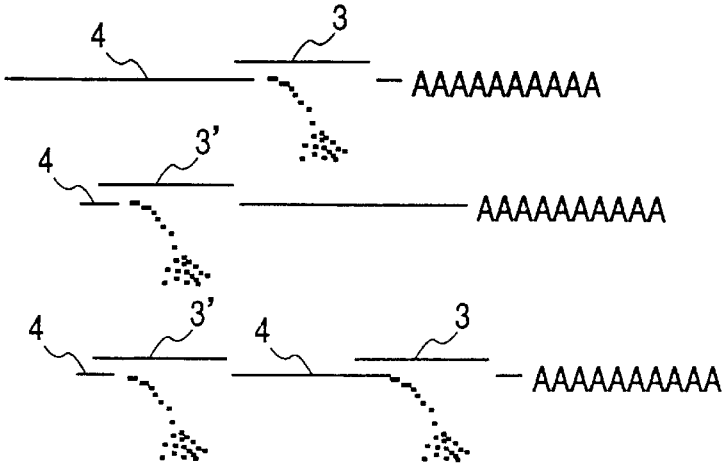

FIG. 3E illustrates the state where the sequence regions of the LEES GENE 2 to which either or both of the probe carriers 3 and 3' are specifically and sufficiently hybridized are digested by the Ribonuclease H. As there are three ways of the hybridization of the probe carriers 3 and 3' in this embodiment, there are three ways of the digestion by the added Ribonuclease H. By the digestion, the LEES GENE 2 is digested in the vicinity of its 3' end to give a fragment 4 as in FIG. 2E. Any of various Ribonuclease H, as well as other enzymes and compounds, as described in FIG. 2E can be employed in the present embodiment.

FIG. 3F illustrates an inactivation treatment of the Ribonuclease H added to the nucleic acid sample; and FIG. 3G illustrates the removal of the probe 3 and/or 3' from the nucleic acid sample by, for example, treating the sample with a DNase.

As described above, the use of plural probe carriers can provide the hybridization between a LEES GENE and probe carriers with higher reliability and hence provide the removal of the LEES GENE with higher efficiency. The species of the probe carriers is naturally not limited to two species, and three or more species of probes can be employed.

As the probe carriers to be used in the present embodiment, those exemplified in the previous embodiment can be used.

Next, the embodiment shown in FIGS. 4A through 4E will now be illustrated:

In this embodiment, cDNA is synthesized from mRNA as the nucleic acid sample prepared in the manner as in FIGS. 2A through 2G.

Figure 4A:
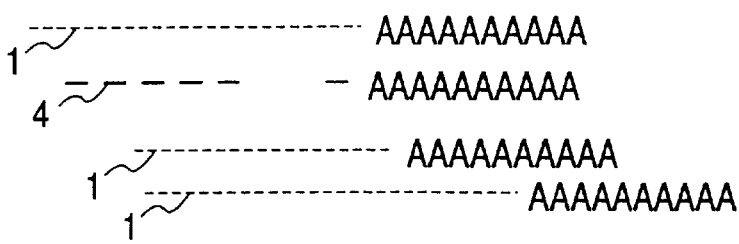

FIG. 4A illustrates the sate of the prepared nucleic acid sample by the above method. To be more specific, in the sample, rare expressed genes 1 which are plural species of mRNAs are coresident with the LEES GENE 4 resulted from the digestion of the LEES GENE 2 in the vicinity of its 3' end.

FIG. 4B illustrates a treatment of adding a primer to the nucleic acid sample to synthesis cDNA. In this embodiment, an oligo (dT) primer is used, whereas the primer to be used depends on a technique for expression analysis. By way of illustration, a primer obtained by adding any of A, G or C to the 3' end of an oligo(dT) primer is, for example, used in the differential display method.

Figure 4C:
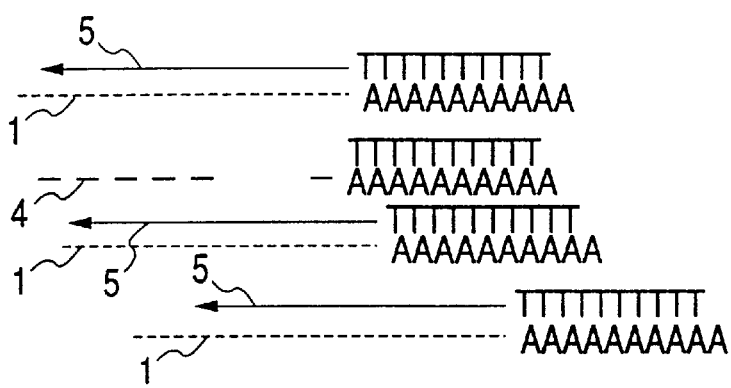

FIG. 4C illustrates the state of a proceeding cDNA synthesis reaction. The cDNA synthesis reaction is conducted using a reverse transcriptase (e.g., Super Script II RT, a product of GIBCO BRL, Gaitherburg, MD., USA). The cDNA synthesis reaction for the rare expressed genes 1 proceeds in a normal manner to give cDNA 5, whereas that for the LEES GENE 4 does not proceed and no cDNA 5 is synthesized. This is because priming site of the LEES GENE 4 is cleaved and removed, and the synthesis reaction ceases at the site of cleavage.

FIG. 4D illustrates a treatment of treating the nucleic acid sample with an RNase to remove RNAs from the sample.

Figure 4E:
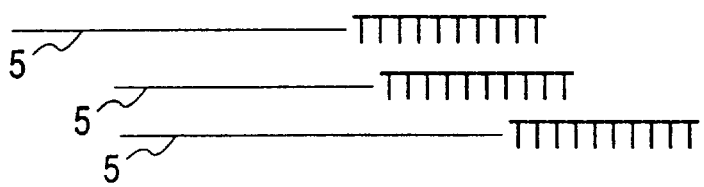

FIG. 4E illustrates the state of the thus-prepared nucleic acid sample composed of cDNA 5 containing no LEES GENE 2.

Detailed description of the technique for synthesizing cDNA from mRNA, the nucleic acid sample obtained in the manner shown in FIGS. 3A through 3G, is omitted herein. In this case, as in FIGS. 4A through 4E, cDNA synthetic reaction ceases at the site that has been digested due to the hybridization with the probe carrier 3 and/or 3' to give a nucleic acid sample composed of cDNA containing no LEES GENE 2.

In the first method mentioned above, the digestion reaction and subsequent treatment steps illustrated in FIGS. 2D through 2G and FIGS. 3D through 3G can be omitted. To this end, for example, a method using a probe carrier (e.g., a ribozyme) having cleaving activity on a hybridized region can be employed. The use of such a carrier to be hybridized with the LEES GENE as shown in FIGS. 2C and 3C naturally results in the state illustrated in FIG. 4A without the procedure of FIG. 2D or FIG. 3D.

Figure 5A:
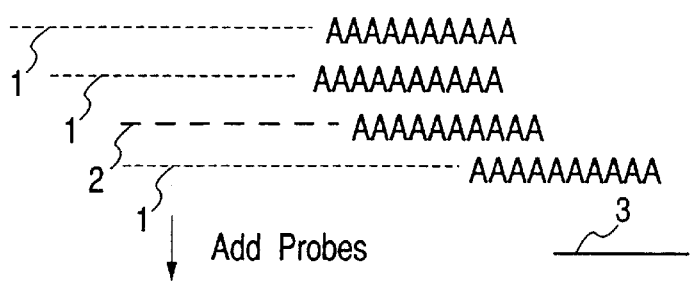

The embodiment illustrated in FIGS. 5A through 5E will now be described below:

FIG. 5A illustrates the sate of a nucleic acid sample composed of mRNAs to be used in this embodiment. The nucleic acid sample is composed of plural species of rare expressed genes 1 to be remained coresident with the LEES GENE 2, as in FIG. 2A.

FIG. 5B illustrates a treatment of adding probe carrier to the provided nucleic acid sample. As the probe carrier 3, use is made of a probe carrier having a sequence hybridizable with the LEES GENE 2 in the vicinity of its 3' end, being designed to have a Tm (melting temperature) of at least equal to, and ideally higher than that of primer for CDNA synthesis, and 3' end of the probe is modified to avoid elongation. The probe carrier may be composed of DNA or its analogue such as PNA (peptide nucleic acid) that has high specificity to the sequence and is resistant against the digestion by a reverse transcriptase. The DNA in this case should be modified with, for example, phosphorothioates since DNA as intact is liable to be digested. The 3' end of the probe carrier can be modified by deoxylation or amination, for instance. The probe carrier to be used in this embodiment should preferably one described in relation with FIG. 2B.

Figure 5C:
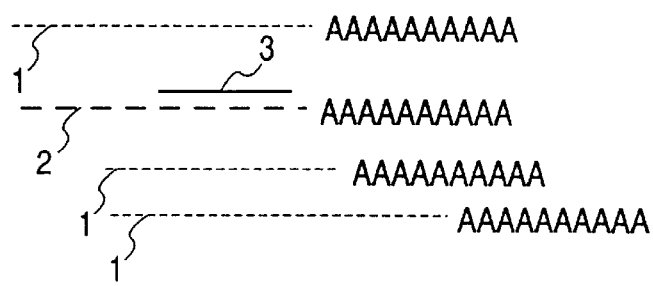

FIG. 5C illustrates the state where the probe carrier 3 is hybridized with the LEES GENE 2 in the provided nucleic acid sample. The hybridization can be conducted in a similar manner as in FIG. 2C.

FIG. 5D illustrates a treatment of adding a primer to the nucleic acid sample to synthesize cDNA. In this embodiment, an example using oligo(dT) primer is employed as in FIG. 4B, whereas the synthetic primer and conditions of cDNA synthetic reaction can be modified as in the aforementioned embodiment.

Figure 5E:
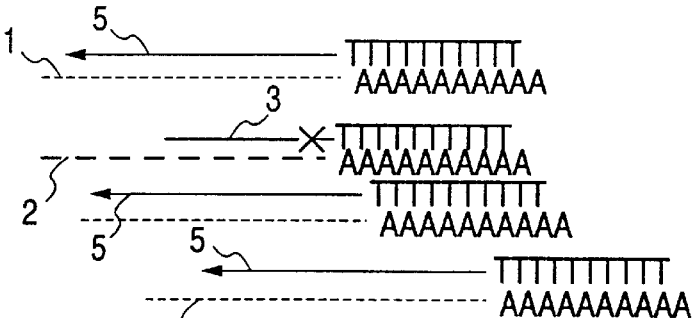

FIG. 5E illustrates the state of a proceeding cDNA synthesis reaction. The cDNA synthesis reaction can be carried out under similar conditions as in FIG. 4C. The synthesis of cDNA 5 from the LEES GENE 2 is inhibited because the probe carrier 3 is hybridized with the LEES GENE 2 in the vicinity of its 3' end.

FIG. 5F illustrates a treatment of removing RNA from the nucleic acid sample by treating the sample with an RNase.

Figure 5G:
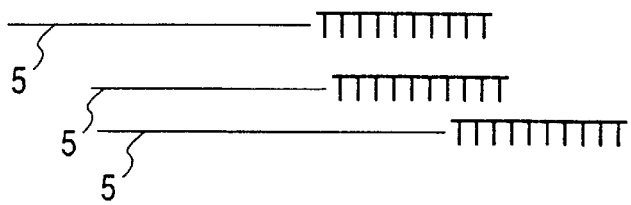

FIG. 5G illustrates the state of the thus-prepared nucleic acid sample composed of cDNA 5 containing no LEES GENE 2.

In this case, the primer for cDNA synthesis is added (FIG. SD) after hybridizing the probe carrier with the LEES GENE (FIG. 5C), whereas cDNA synthesis can be conducted after adding the probe carrier 3 and the primer concurrently to the sample and then allowing the reaction condition to meet the hybridization condition. The bond between the probe carrier and LEES GENE is made through hydrogen bonds in this case, whereas it may also be conducted by, for example, providing a photo affinity labeled probe carrier 3 and hybridizing it with the LEES GENE 2 and then allowing the LEES GENE and probe carrier to combine with each other through covalent bonds by light irradiation. A similar probe carrier as demonstrated with reference to FIG. 2B can be employed as the probe carrier in this embodiment.

Next, the second method according to the invention will be described in detail with reference to FIGS. 6A though 6F. The second method is characterized by immobilizing a probe on a solid phase. As the nucleic acid sample, any of mRNAs and first strand cDNAs can be employed. The sequence of the probe can be directed to any of regions in the LEES GENE, but when the region to be analyzed in the expression analysis is expected, a probe coding for the identical region with the target region should preferably be employed. By taking the differential display method as example, the 3' region is analyzed and hence a probe coding for 3' region is to be used. The solid phase for immobilizing the probe can have any configuration, such as in the form of bead, glass plate or microtube. It should immobilize the probe with high density and the adsorption of DNA by its surface should be minimized. The use of beads, in particular, of magnetic beads will be described in this embodiment.

FIG. 6A illustrates a treatment of providing a solution 12 containing a target nucleic acid sample in a microtube 11. The nucleic acid sample may be composed of mRNAs or total RNA, as in described with reference to FIG. 2A. The sample contains LEES GENE 16 with plural rare expressed genes 15 to be remained.

FIG. 6B illustrates a treatment of preparing bead 13 onto which probe carrier 14 being complementary to the LEES GENE 16 is immobilized. As the bead, commercially available beads such as Dynabeads (registered trade mark; DYNAL CORPORATION, Oslo, Norway) and BioMag (Perseptive Biosystems, Bedford, Mass., USA) can be employed. The immobilization can for example be conducted in the following manner: Probe 14 whose 5' end is biotinylated is synthetically obtained, and mixed with beads whose surfaces are coated with streptavidin in a buffer to immobilize the probe onto the beads through avidin-biotin bonds.

FIG. 6C illustrates a treatment of mixing the provided immobilized probe 14 with the nucleic acid sample 12 in the microtube 11, allowing the reaction mixture under conditions suitable for hybridization (the conditions can be referred to those in the first method), and specifically hybridizing the LEES GENE 16 with the probe 14. Consequently, the LEES GENE 16 is hybridized with the probe 14 and thus captured onto the surfaces of beads, whereas the rare expressed genes 15 to be remained are including in the nucleic acid sample.

FIG. 6D illustrates a treatment of collecting beads cluster 17 to an area of the microtube 11 with the use of a magnet.

FIGS. 6E and 6F illustrate a treatment of remaining the beads cluster 17 in the microtube 11 and migrating the nucleic acid sample after reaction into another microtube 18.

As a result of the above treatments, a nucleic acid sample composed of mRNAs or cDNAs containing no LEES GENE is recovered in the microtube 18.

Figure 7:
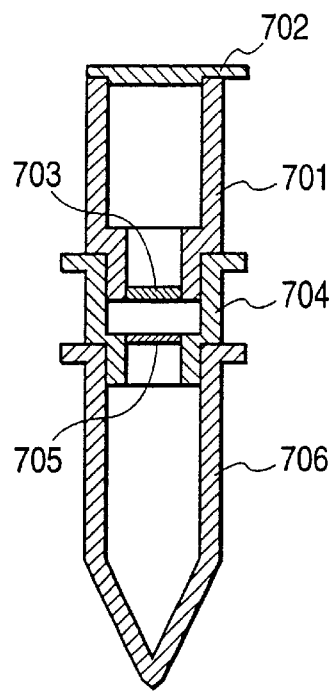
FIG. 7 is a cross sectional view illustrating an embodiment of an apparatus which is useful for the recovery of nucleic acid samples not immobilized on a probe as in embodiments according to the invention.
Figure 8A:
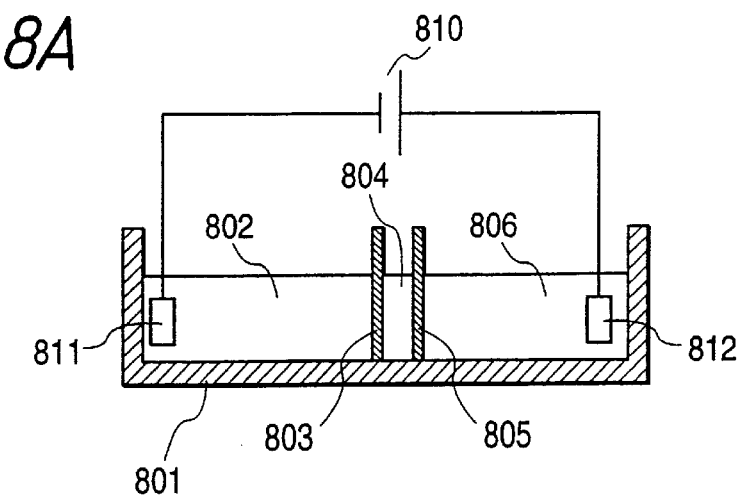
FIGS. 8A and 8B graphically illustrate, respectively, a sectional view and usage of, and a plane view of another embodiment of an apparatus which is useful for the recovery of nucleic acid sample not hybridized with a probe in the embodiments according to the invention.
Figure 8B:
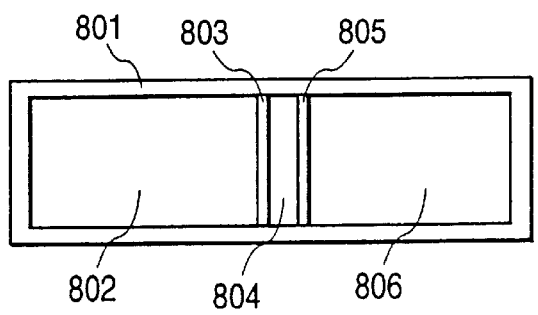

FIG. 7 and FIGS. 8A and 8B respectively illustrate apparatus useful for another embodiment of the treatment shown in FIGS. 6D through 6F.

FIG. 7 demonstrates a centrifuge tube having dual-membrane structure as the apparatus. First chamber 701 is equipped with a lid at the top and membrane filter 703 at the bottom. The membrane filter 703 has a configuration for retaining the probe 14 physically or chemically. As the membrane filter, use can be made of membranes each composed of a structure having sufficient pore size to allow nucleic acids to permeate therethrough, but not to allow nucleic acids hybridized with a probe which is immobilized onto, for example, bead to permeate physically therethrough; or membranes using a substance having affinity to the probe, such as a streptavidincoated membrane to which biotinylated probe can be bound. The top of second chamber 704 is engaged to the lower part of the first chamber 701, and the chamber 704 is provided with membrane filter 705 in its inside. As the membrane filter 705, use can be made of filters that can retain nucleic acids but allow water and inorganic salts to permeate therethrough to concentrate the nucleic acids, such as conventional ultrafilters. The top of third chamber 706 is engaged to the bottom of the second chamber 704. Centrifuge tubes having analogous structure to that of the above centrifuge tube include, for example, Micropure EZ and Microcon (trande names; Amicon, Danvers, Mass., USA).

Upon the three chambers being assembled, the nucleic acid sample prepared by the aforementioned methods is put into the first chamber 701, and centrifuged by proper centrifugal force; then, the LEES GENE 16 hybridized with the probe which is immobilized onto, for example, beads remains in the first chamber 701, and the rare expressed genes 15 are captured within the second chamber 704. Naturally, LEES GENEs which cannot be hybridized with the probe 14 remain with the rare expressed gene 15 in the second chamber 704. Into the third chamber 706 is collected unnecessary liquid.

The genes captured in the second chamber 704 are composed of not only the rare expressed genes 15 but also LEES GENEs which cannot be hybridized and treated with the probe 14, and the residual LEES GENEs should be treated with another probe. This treatment process will be described later.

FIGS. 8A and 8B illustrate a sectional view and a plane view, respectively, of another embodiment in which the isolation of genes is carried out not by centrifuge but by electrophoresis. Electrophoresis cell 801 is provided in its inside with membrane filters 803 and 805. The membrane filter 803 may have the same configuration as the membrane filter 703, whereas the membrane filter 805 may have the same configuration as the membrane filer 705. The inside of the electrophoresis cell 801 constitutes three cells 802, 804 and 806 respectively divided by the membrane filters 803 and 805. The left end of the cell 802 is provided with electrode 811, and the right end of the cell 806 is provided with electrode 812. To each of the electrodes is supplied a given electric potential from power source 810.

The nucleic acid sample prepared by the aforementioned method is placed into the cell 802, and a proper buffer is put into the cells 804 and 806. When the amount of the nucleic acid sample in the cell 802 is small, the buffer should preferably be put into the cell 802. Upon supplying a given electric potential from the power source 810, the LEES GENE 16 hybridized with the probe which is immobilized onto, for example, beads remains in the cell 802, and the rare expressed gene 15 is captured in the cell 804. Naturally, LEES GENEs not hybridized with the probe 14 remain with the rare expressed genes 15 in the cell 804.

The genes captured in the cell 804 are composed of not only the rare expressed gene 15 but also LEES GENEs which cannot be hybridized with the probe 14, and the residual LEES GENEs should be treated with another probe, as in the embodiment shown in FIG. 7.

In the configurations illustrated in FIG. 7 and FIGS. 8A and 8B, the driving force to collect genes to the second chamber 704 or to the cell 804 is not limited to those shown in the above embodiments. The genes can also be collected by transferring the sample solution physically with, for instance, a pump.

Next, the third method will be described in detail with reference to FIG. 9. The third method is a technique to enhance the precision of removal in the first and second methods. It is preferable to remove all LEES GENEs by treating once, but it may not be always successful. In order to remove plural LEES GENEs with high precision, it is effective to remove the LEES GENEs while detecting the removal of individual LEES GENEs. According to the third method, therefore, the extent of removal in the recovery obtained by the first method or second method is monitored, and a successive removing process of genes to be removed is conducted according to necessity.

Figure 9:
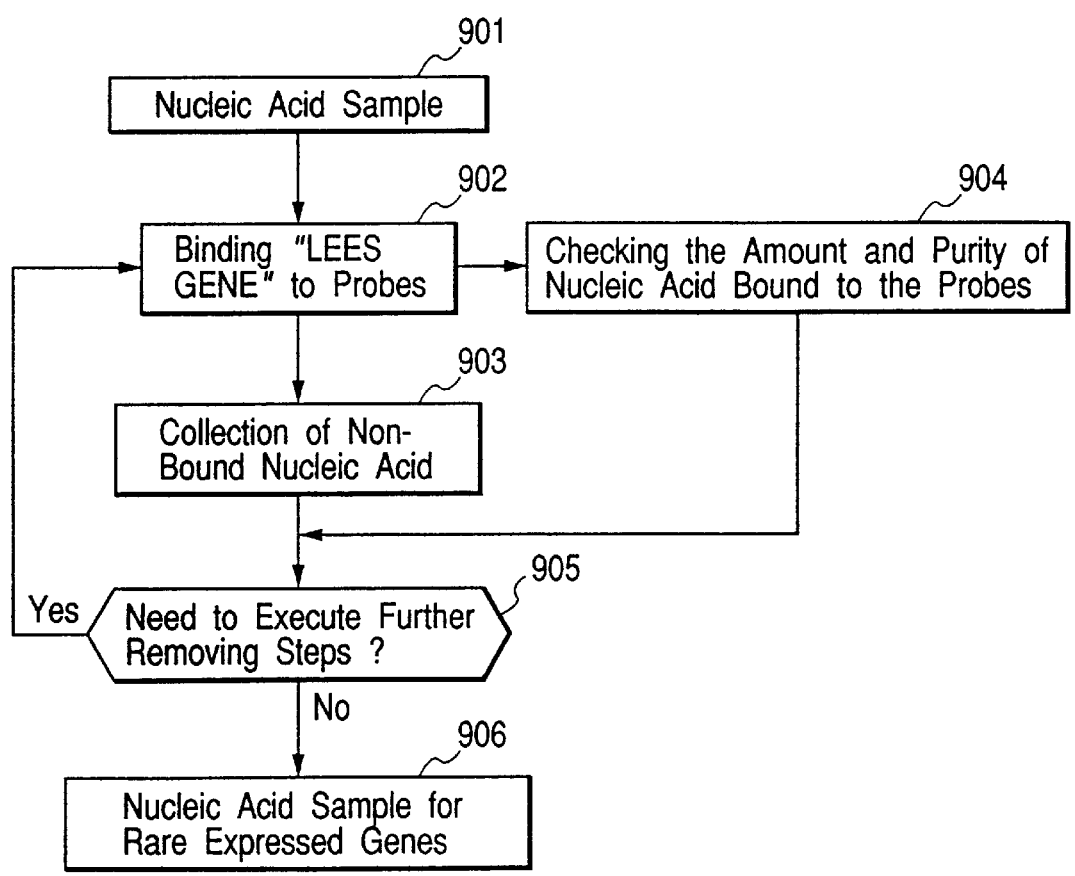
FIG. 9 graphically illustrates the flow of a further embodiment according to the invention of the steps for obtaining a nucleic acid sample predominantly composed of rare expressed genes from a nucleic acid samples to be analyzed.

FIG. 9 illustrates an embodiment for enhancing the precision of the resultant sample obtained by the second method. Step 901 is a step for providing a nucleic acid sample, step 902 is a step for hybridizing probe carriers with LEES GENE and step 903 is a step for the collection of nucleic acid sample containing non-hybridized genes, and these steps are conducted in a similar manner as in the second method.

Step 904 is a step for checking the amount and purity of nucleic acids hybridized with the probe. By taking the embodiment using the beads 13 as illustrated in FIG. 6A through 6F, the step 904 is conducted in the following manner: To the bead cluster 17 shown in FIG. 6E (the bead cluster after the recovery of nucleic acid sample) is added a buffer, and the mixture is heated to denature the hybridized genes. The denatured LEES GENE is quantified by, for example, RT-PCR (reverse transcriptase-PCR, refer for example, FEBS Letters (1994) 231–236). Step 905 is a step for the judgment whether the removing step should be repeated or not, in which the necessity of repeat of the removing step is judged depending on the result of quantification obtained in the step 904.

Conducting this judgment means the removing step should be repeated until the LEES GENE contained in the recovered nucleic acid sample have an equivalent concentration to that of the rare expressed genes. The judgment can be carried upon the collected non-hybridized nucleic acid sample. When the repetition of the removing step is judged necessary, the steps 902 to 903 are repeated. When it is judged unnecessary, a nucleic acid sample predominantly composed of rare expressed genes is obtained, as illustrated in step 906. To be more specific, once the LEES GENE has an equivalent concentration to those of rare expressed genes, genes which are originally rare expressed genes become major genes occupying sufficient parts of the nucleic acid sample.

By repeating the removing step while quantifying the LEES GENEs as described above, the precision of removal can be enhanced. The use of a DNA tip composed of arrayed LEES GENE as the probe carrier instead of beads can provide real-time quantitation of the LEES GENEs.

As thus described, gene analysis is conducted on a nucleic acid sample predominantly composed of target rare expressed genes and hence the results of analysis with high precision can be obtained.

The present invention will be further illustrated with reference to the following verification experiment which is not directed to limiting the scope of the invention.

Verification Experiment

To verify the effectiveness and advantages of the preparation of a nucleic acid sample predominantly composed of rare expressed genes as in the present invention, effects of the presence of a LEES GENE on the analysis of rare expressed genes were examined. As an experimental material, ten murine genes having different sizes yet having the same sequences at both ends were used. A series of nucleic acid samples in which the amount of one species of gene (gene H) of ten species (from gene A to gene J in decreasing order of molecular weight) were prepared, and subjected to analysis according to the differential display method using the sequences of the both ends. The analysis will be illustrated in detail below.

The nucleic acid sample was prepared in the following manner. Initially, the ten murine genes were prepared as follows as follows: According to the fluorescent differential display method (Takamichi Muramatsu, *Protocols for PCR Experiments of Plants,* new edition, 138–143, Shujun-sha, Japan), murine RNAs were isolated on electrophoresis, ten genes, genes A through H having different sizes were cut from gel and cloned to a vector (pGEM-T vector System; Promega, Madison, Wis., USA) respectively. Plasmid to be used herein was purified using a commercially available kit (RPM kit; BIO 101 Inc., Calif., USA). Using the purified plasmid as a template, genes A through J were respectively amplified by subjecting to PCR (AmpliTaq and GeneAmp PCR System 9600; Perkin-Elmer, Norwalk, Conn., USA) according to a conventional method using universal primers (Sequence Listing: Sequence ID Nos. 1 and 2). The PCR product was purified using QIAquick PCR Purification Kit (QIAGEN Inc Chatsworth, Calif., USA) and subjected to quantitative analysis with a spectrometerEii (U-3210, Hitachi Ltd., Japan). Using individual quantified genes, two series of samples, a total of 12 samples, in each series other genes than gene H were constant in amount and the gene H (LEES GENE) was present as much in amount as the other genes by a factor of 1, 100, 500, 1,000, 5,000 and 10,000. Table 1 demonstrates the compositions of the nucleic acid samples.

TABLE 1

Composition Ratios of the Nucleic Acid Samples (mol/µl)

| Lane | 1 | 2 | 3 | 4 | 5 | 6 |
|---|---|---|---|---|---|---|
| Ratio of LEES GENE | 1 | 100 | 500 | 1000 | 5000 | 10000 |
| Other genes | $1 \times 100^{-20}$ | $1 \times 100^{-20}$ | $1 \times 100^{-20}$ | $1 \times 100^{-20}$ | $1 \times 100^{-20}$ | $1 \times 100^{-20}$ |
| Gene H | $1 \times 100^{-20}$ | $1 \times 100^{-18}$ | $1 \times 100^{-18}$ | $1 \times 100^{-17}$ | $1 \times 100^{-17}$ | $1 \times 100^{-16}$ |
| Lane | 7 | 8 | 9 | 10 | 11 | 12 |
| Ratio of LEES GENE | 1 | 100 | 500 | 1000 | 5000 | 10000 |
| Other genes | $1 \times 100^{-18}$ | $1 \times 100^{-18}$ | $1 \times 100^{-18}$ | $1 \times 100^{-16}$ | $1 \times 100^{-18}$ | $1 \times 100^{-18}$ |
| Gene H | $1 \times 100^{-18}$ | $1 \times 100^{-16}$ | $1 \times 100$ | $1 \times 100^{-15}$ | $1 \times 100^{-15}$ | $1 \times 100^{-14}$ |

(Amplification of the Nucleic Acid Samples by PCR)

The primer used for the amplification is as follows: anchor primer: Sequence listing: sequence ID No. 3 Arbitrary primer (OPERON TECHNOLOGY, Inc., Alameda, Calif., USA): Sequence listing: sequence ID NO. 4

The sequences of the above primers were present identically at the both ends of the genes A through J. At the 5' end of the anchor primer was labeled with a fluorescent substance (Texas-Red) for the purpose of detection.

A reaction mixture for PCR was prepared according to the fluorescent differential display method in the following manner:

Table 2 demonstrates the composition of a material mixture.

TABLE 2

| Composition of Material Mixture | |
|---|---|
| 2.5 mM dNTP (Nippon Gene Co., Ltd., Japan) | 0.4 µl |
| 10 x GeneTaq Buffer (Nippon Gene Co., Ltd., Japan) | 2.0 µl |
| anchor prmer (1 µM) | 5.0 µl |
| Arbitrary primer (10 µM) | 1.0 µl |
| GeneTaq (Nippon Gene Co., Ltd., Japan) | 0.1 µl |
| AmpliTaq (Perkin-Elmer) | 0.1 µl |
| Distilled water | 10.4 µl |
| Total | 19 µl |

To 1 µl each of the nucleic acid samples 1 to 12 was added 19 µl of the mixture shown in Table 2 to give a series of PCR reaction mixtures (20 µl). The temperature cycle of PCR was set as follows: The first cycle was composed of 94° C. for 3 min, 40° C. for 5 min and then 72° C. for 5 min in this order, and a subsequent cycle was composed of 94° C. for 20 sec, 40° C. for 2 min and then 72° C. for 1 min in this order, and this subsequent cycle was repeated a total of 24 times, followed by a reaction at 72° C. for 5 min.

Detection of PCR Products

To 2.0 µl of the PCR product was added an equivalent volume of a loading buffer (98% formamide, 10 mM EDTA, 0.01% Methyl Violet) and the resultant mixture was treated at 80° C. for 2 min to give a sample. The sample was subjected to electrophoresis on a denatured acrylamide gel (6% Long Ranger (FMC Corp., Rockland, Md., USA), 6.1

M urea, 1.2 xTBE) and then to detection with a fluorescence image scanner (FMBIO, TaKaRa, Japan).

Figure 10:
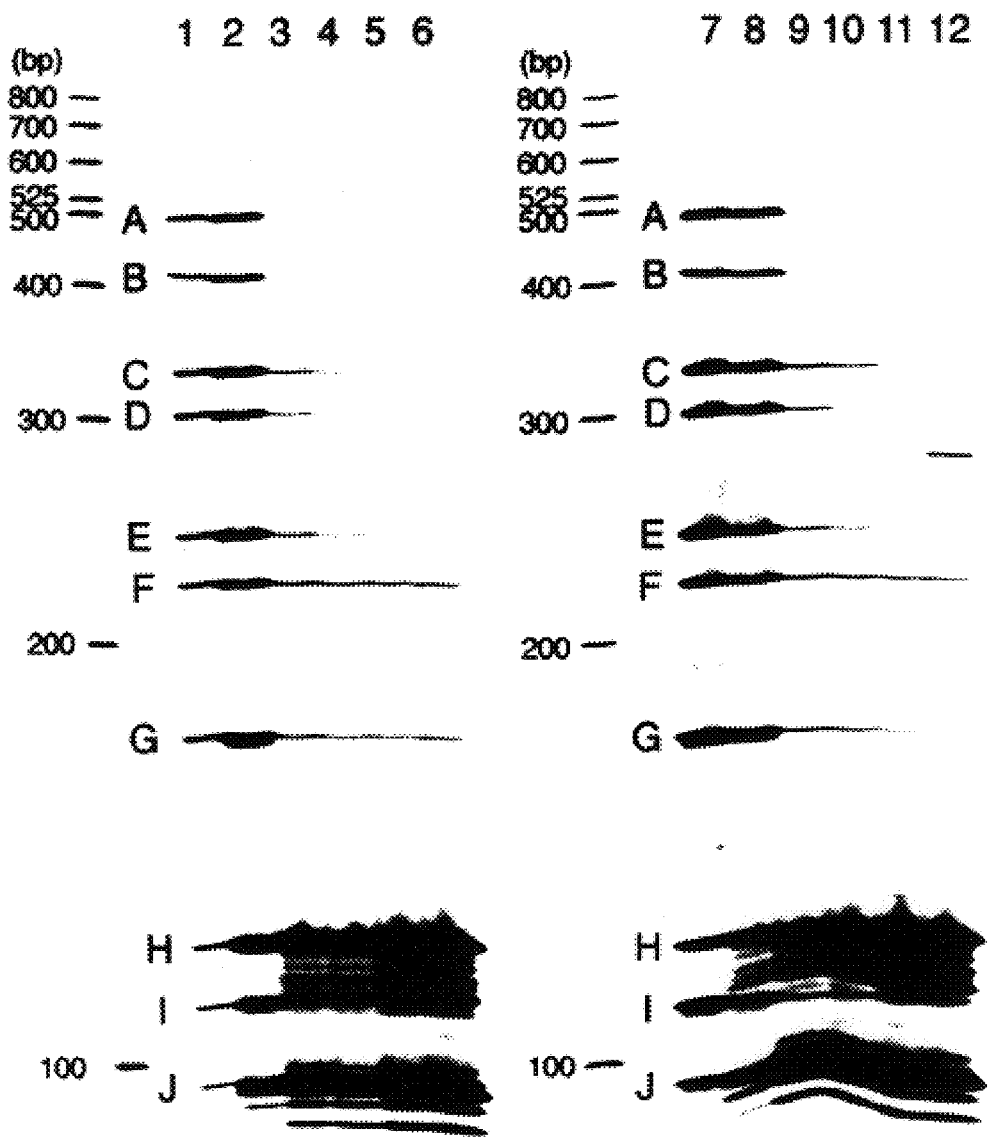
FIG. 10 is a photograph illustrating the result of electrophoresis on an acrylamide gel to verify the advantages of the invention.

FIG. 10 demonstrates the results of above detection, in which lanes 1 through 12 are respectively the results of isolation of the PCR products of the nucleic acid samples 1 through 12 shown in Table 1. Lanes 7 through 12 correspond to the nucleic acid samples containing genes 100 times as much as those of the lanes 1 through 6, respectively. Bands A through J respectively indicate products of the individual genes A thorough J. The numerals 100 through 800 indicate base lengths (bp) of molecular weight markers.

The lanes 1, 2 and 7, 8 correspond to the reaction products of the nucleic acid samples containing gene H in an equivalent amount and 100 times as much as the other genes, indicating that all genes were amplified uniformly. The lanes 3, 4, 5, 6 and 9, 10, 11, 12 demonstrate the results of the nucleic acid samples containing gene H 500 times or more as much as the other genes. The bands A, B, C, D, E, F, G, I and J in these lanes are apparently thin than those in the lanes 1, 2 and 7, 8, although the nucleic acid samples 1 through 6 and 7 through 12 respectively contained equivalent amount of the other genes than gene H, indicating that uniform gene amplification is inhibited.

The above results indicate that the presence of a gene belonging to the abundant class (gene H) in a nucleic acid sample inhibits the detection of genes belonging to the rare class (genes A, B, C, D, E, F, G, I and J), and that contrary to this, removal of an abundant gene (gene H) from a nucleic acid sample containing largely different amounts of genes enables the detection of rare expressed genes (genes A, B, C, D, E, F, G, I and J).

In comparison between the lanes 1 through 6 and lanes 7 through 12, the results were almost equivalent though the latter nucleic acid samples contained genes 100 times as much as those in the former nucleic acid samples, indicating that even if the absolute amounts of rare expressed genes are increased, the amplification of the genes is inhibited as far as an abundant gene is present in a sample.

The results of the verification experiment above indicate that the removal of an abundant gene from a nucleic acid sample is effective in the expression analysis of rare expressed genes. the advantages of this technique were examined using a detection method with the use of PCR technique in the experiment, whereas similar advantages can presumably be obtained as long as a technique with hybridization of a probe or primer is used for the analysis of expressed amounts.

As described above, genetic diagnoses for studying mutation of genes have been conducted, whereas studies upon the relationship between RNA profiling verifying, in general, the expression styles of mRNAs and diseases have been launched. It is expected that genetic diagnoses utilizing such RNA profiling will be established in near future. A candidate sample for the RNA profiling is a tissue presenting with a symptom, but the practical preparation of mRNA by subjecting a patient to tissue biopsy is attended with technical difficulties and pain of the patient. Separately, the use of peripheral blood as a sample is advantageous for expected application to prophylaxis diagnosis. In this case, the application of the present invention to a nucleic acid samples obtained from peripheral blood is important and such an expanded application can be realized, as described below.

The peripheral blood contains a large quantity of blood cells such as red blood cells, white blood cells and platelets, and, occasionally, trace amounts of othercells such as metastatic tumor cells. When plural species of cells are present in co-existence, more complicated gene expression is expected, and the problems caused by deference in expression amounts should be solved to obtain accurate information particularly on rare expressed genes. Consequently, the present invention is effective for gene expression analysis for the purpose of genetic diagnosis using peripheral blood. The species and amounts of major blood cells are described in "*Molecular Biology of the Cell,* 3rd edition, p1164 (Kyoiku-sha K. K., Japan)". Of these blood cells, targets to be analyzed are white blood cells other than red blood cells and platelets both of which have no nuclei. The aforementioned database BodyMap demonstrates the species and expression amounts of expressed genes in major white blood cells such as granulocytes and T cells ($CD4^+T$ cell, $CD8^+T$ cell) through incidences obtained by sequencing at random 500 to 1000 cDNAs prepared from individual tissues. On condition that the total expressed gene in a cell is about 300,000, a gene having an incidence of 1 corresponds to gene expression of about 300 to 600 copies. The present invention can therefore be applied to genetic diagnosis of peripheral blood, defining the LEES GENEs as the genes each having an incidence of equal to or more than 2 (600 to 1200 copies) from among genes in the database of granulocytes and T cells ($CD4^+T$ cell, $CD8^+T$ cell). Nucleic acid samples prepared from peripheral blood according to the invention can also be applied to genes not being present by nature on human genome. The applications include, for instance, high-sensitivity diagnosis of infectious diseases by pathogen having RNA as its genome such as retrovirus.

The present invention provides preparation methods of nucleic acid samples which enable concurrent analyses of rare expressed genes, and analyzing methods based upon the nucleic acid samples. Such concurrent analyses of rare expressed genes should become more important in future. The methods. according to the invention are novel methods of removing abundant genes, whereas most of conventional methods for analyses of rare expressed genes are of improving the sensitivity of detection.

What is claimed is:

1. An apparatus for removing one or plural genes hybridized with probes from a mixture of one or plural abundant expressed genes hybridized with probes and rare expressed genes not hybridized with probes, comprising:
    a first chamber having a lid at a top part and a first membrane filter at a lower part, a solution containing a mixture of one or plural abundant expressed genes hybridized with the probes is added into said first chamber, said first membrane filter chemically or physically retaining said abundant expressed genes hybridized with the probes, and said first membrane filter having a pore size permeating said rare expressed genes not hybridized with the probes therethrough;
    a second chamber having a second membrane filter at a lower part and coupled to a lower part of said first chamber, said second membrane filter not permeating said rare expressed genes not hybridized with the probes and permeating water and inorganic salts therethrough to concentrate said rare expressed genes not hybridized with the probes; and
    a third chamber coupled to a lower part of said second chamber, substances permeated through said second membrane filter being collected into said third chamber;
    wherein said abundant expressed genes hybridized with the probes remain in said first chamber and said rare expressed genes not hybridized with the probes remain in said second chamber.

2. An apparatus according to claim 1, wherein the probe is immobilized on a solid substance and said first membrane filter does not permeate the solid substance.

3. An apparatus according to claim 2, wherein the solid substance is a bead.

4. An apparatus according to claim 1, wherein the probes are biotinylated probes and said first membrane filter is streptavidin-coated membrane.

5. An electrophoresis cell for removing one or plural genes hybridized with probes from a mixture of one or plural abundant expressed genes hybridized with probes and rare expressed genes not hybridized with probes, comprising:
    a first cell in which a buffer solution is contained and a first electrode is provided;
    a second cell in which the buffer solution is contained; and
    a third cell in which the buffer solution is contained and a second electrode is provided;
    wherein said first cell and said second cell have a common first membrane filter for dividing said first cell and said second cell, said second cell and said third cell have a common second membrane filter for dividing said second cell and said third cell, a solution containing a mixture of one or plural abundant expressed genes hybridized with probes and rare expressed genes not hybridized with the probes is added into said first cell, said common first membrane filter chemically or physically retaining said abundant expressed genes hybridized with the probes, and said common first membrane filter having a pore size permeating said rare expressed genes not hybridized with the probes therethrough;

wherein said common second membrane filter do not permeate said rare expressed genes not hybridized with the probes; and wherein, by supplying an electric potential between the first and second electrode and performing electrophoresis for migrating said rare expressed genes not hybridized with the probes from the first cell to the second cell, said abundant expressed genes hybridized with the probes remain in said first cell, and said rare expressed genes not hybridized with the probes remain in said second cell.

6. An electrophoresis cell according to claim 5, wherein the probes are immobilized on a solid substance and said common first membrane filter does not permeate the solid substance.

7. An electrophoresis cell according to claim 6, wherein the solid substance is a bead.

8. An electrophoresis cell according to claim 6, wherein the probes are biotinylated probes and said first common membrane filter is streptavidin-coated membrane.

* * * * *

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA
```

-continued

```
<400> SEQUENCE: 1
aaagggggat gtgctgcaag gcg                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
gcttccggct cgtatgttgt gtg                                            23

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3 gtttttttt tttttg                                                     17

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ggtctggttg                                                           10
```